United States Patent [19]

Ogunbiyi et al.

[11] Patent Number: 4,537,746

[45] Date of Patent: Aug. 27, 1985

[54] METHODS FOR DISINFECTING AND PRESERVING CONTACT LENSES

[75] Inventors: Lai Ogunbiyi, Fairport; Francis L. Scott, Rochester; Francis X. Smith, Walworth, all of N.Y.

[73] Assignee: Bausch & Lomb Incorporated, Rochester, N.Y.

[21] Appl. No.: 566,833

[22] Filed: Dec. 29, 1983

[51] Int. Cl.$^3$ .............................................. A61L 2/16
[52] U.S. Cl. .......................................... 422/28; 422/37
[58] Field of Search ......... 134/42; 252/106, DIG. 14; 422/28, 37; 424/326

[56] References Cited

U.S. PATENT DOCUMENTS

| | | | |
|---|---|---|---|
| 4,013,576 | 3/1977 | Loshack | 422/37 |
| 4,354,952 | 10/1982 | Riedhammer et al. | 252/DIG. 14 |
| 4,388,229 | 6/1983 | Fu | 252/DIG. 14 |

FOREIGN PATENT DOCUMENTS 1432345  4/1976  United Kingdom ................ 424/326

*Primary Examiner*—Ivars Cintins
*Attorney, Agent, or Firm*—Bernard D. Bogdon; Gregory E. Croft

[57] ABSTRACT

Improved methods of disinfecting and/or preserving contact lenses comprises treating said lenses with an effective concentration of a solution comprising a biguanide or a water soluble salt of the formula:

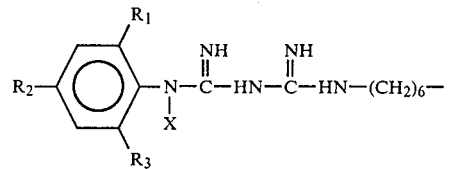

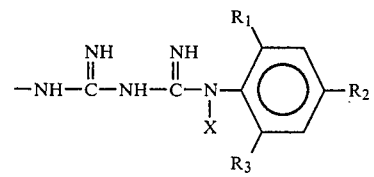

wherein $R_1$ and $R_3$ are selected hydrogen, halogen, alkyl, alkoxy, nitro, $-SO_2R_4$, carboxyl or hydroxyl where $R_4$ is $-NH_2$, $-NHR'$, $-NR'R''$, $-OR'$ or $-O$—aryl in which $R'$ and $R''$ are alkyl or alkoxy; $R_2$ is hydrogen or halogen and X is hydrogen or alkyl, provided that when $R_2$ is halogen then both $R_1$ and $R_3$ are hydrogen and X is alkyl. The method provides for disinfecting and/or preserving contact lenses wherein the monomeric biguanide-containing solutions offer a wide spectrum of antimicrobial activity with nominal binding and concentrating onto lens surfaces and low levels of eye tissue irritation or inflammation.

19 Claims, No Drawings

METHODS FOR DISINFECTING AND PRESERVING CONTACT LENSES

BACKGROUND OF THE INVENTION

This invention relates generally to improved methods for disinfecting and/or preserving contact lenses and contact lens care solutions. The solutions contain monomeric biguanides as their prinicpal active disinfecting agent, perform with a low level of residual binding or concentrating onto lens surfaces and exhibit low toxicity levels. The solutions described herein are compatible for use with other germicidal agents for solution preservation, as well as for complimenting or broadening the spectrum of microbicidal activity. In some instances, lower concentrations of such agents may be used, further reducing the risk of residual build-up on soft contact lenses and incidents of eye tissue irritation and inflammation.

Generally, contact lenses in wide use fall into two categories: the hard or rigid corneal type lenses formed from materials prepared by polymerization of acrylic esters, such as polymethyl methacrylate (PMMA), and gel, hydrogel or soft type lenses made of polymerized hydrophilic or hydrophobic monomers, such as 2-hydroxyethyl methacrylate (HEMA). The hard acrylic type contact lenses are characterized by low water vapor diffusion constants, resistance to the affects of light, oxygen and hydrolysis and absorb only minor amounts of aqueous fluids. Because of the durability of hard contact lenses coupled with their tendency not to absorb appreciable amounts of water, the selection of suitable disinfecting agents, cleaning agents or other lens care compounds is relatively non-critical.

However, unlike hard lenses, soft type contact lenses and certain of the newer gas permeable hard contact lenses have a tendency to bind and concentrate significantly more fluids, environmental pollutants, water impurities, as well as antimicrobial agents and other active ingredients commonly found in lens care solutions. In most instances, the low levels of such ingredients in lens care solutions does not lead to eye tissue irritation when used properly. Nevertheless, because of the inherent binding action of protein deposits and soft lens materials disinfecting agents and preservatives tend to build up on lens surfaces, and become concentrated to potentially hazardous levels, such that when released can cause corneal inflammation and other eye tissue irritation.

Previous efforts to alleviate the problem of binding and concentrating disinfectants and preservatives onto contact lens surfaces, and reducing the potential for eye tissue irritation have not been totally satisfactory. For example, in spite of low toxicity levels not all disinfectants are compatible for use with all types of contact lenses. Many hard lens disinfecting and preservative solutions contain benzalkonium chloride or chlorobutanol. Although they are effective antibacterial agents, their use can result in a loss of lens hydrophilic properties, cause solution instability or may even lack compatibility with certain types of hard lenses, e.g. high silicon content.

Other antibacterial agents were found to be more compatible with contact lenses and exhibit less binding on lens surfaces. U.S. Pat. No. 4,361,548 discloses a contact lens disinfectant and preservative containing dilute aqueous solutions of dimethyldiallylammonium chloride (DMDAAC) wherein amounts of DMDAAC as low as 0.00001 percent by weight are employed when an enhancer, such as thimerosal, sorbic acid or phenylmercuric salt are used therewith. Although lens binding and concomitant eye tissue irritation with DMDAAC were reduced, it was found in some users to be above desirable clinical levels.

Other efforts to reduce or eliminate soft lens binding have led to the use of anti-binding or detoxifying agents, like polyvinyl pyrrolidone (PVP) and polyvinyl alcohol (PVA). However, these polymers alone were found to be ineffective, for the most part, in reducing lens binding and eye tissue irritation.

Heretofore, monomeric biguanides have been used in lens disinfecting and preservative solutions. For example, the biguanide chlorhexidine was reported by B. S. Plant et al in the *J. Pharm. Pharmacol.*, 32, 453–459 (1980) suggesting its use as a disinfectant with soft contact lenses. It was discovered, however, that chlorhexidine was absorbed to some extent by such lenses and was therefore not an ideal agent for such systems. One solution to this problem is suggested by U.S. Pat. No. 4,354,952 which discloses very dilute disinfecting and cleaning solutions containing chlorhexidine or its salts in combination with certain amphoteric and nonionic surfactants. Although these solutions are effective in reducing binding properties, their antimicrobial activity may be diminished when used with certain amphoteric surfactants. In the case of chlorhexidine, it was found that if not used in the proper ratio the surfactant and disinfectant will precipitate unless a combination of surfactants are employed.

While it has been reported that more conventional chlorhexidine-containing disinfectant solutions bind to soft contact lenses seven times less than benzalkonium chloride, the presence of proteinaceous oily, tear-film deposits can double the amount of chlorhexidine absorbed over that of clean lenses.

Other efforts to alleviate the problem of contact lens binding and eye tissue inflammation are disclosed in copending U.S. application Ser. No. 528,322, filed Aug. 31, 1983. There, water soluble polymeric biguanides having molecular weights of up to 100,000 were found to demonstrate an unusually low level of absorption and residual build-up on contact lens surfaces. It was discovered, for example, that polyhexamethylene biguanides could be used at extremely low levels in contact lens disinfecting solutions while providing a broad spectrum of microbicidal activity, substantially free of binding effects and without prompting a cytotoxic response.

It was also quite surprising to have found that not only did the polymeric biguanides demonstrate unusually low levels of lens absorption, binding and toxic response, but the monomers of such polymers also performed comparably. This was rather unexpected in view of past efforts to solve the aforestated problem have generally shown that polymers, and usually higher molecular weight materials, provided the lowest levels of lens absorption and binding activity. That is to say, heretofore, it was generally held that polymeric type disinfectants offered the most probable rationale for solving the problem of lens binding and eye tissue irritation, since their molecules were less likely to penetrate lens micropores than their monomeric counterparts. Hence, the present invention provides for an improved and unexpected new means for treating contact lenses. The solutions are compatible for use with both hard and soft type lenses, and are adaptable for use with virtually any of the commonly known disinfecting techniques, including "cold" soaking under ambient temperature conditions, as well as with high temperature disinfecting methods. The disinfecting and preservative solutions employed according to the methods described herein are especially noteworthy for their wide spectrum of bactericidal and fungicidal activity, at low concentrations coupled with low toxicity levels and reduced affinity for binding and concentrating when used with soft type contact lenses.

SUMMARY OF THE INVENTION

In accordance with this invention, there is provided a method for disinfecting and/or preserving contact lenses which comprises contacting said lenses with an antimicrobial amount of a solution of a biguanide or water-soluble salt thereof having the following general formula:

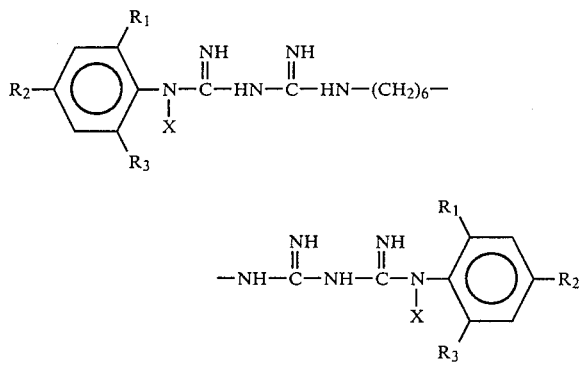

wherein $R_1$ and $R_3$ are independently selected from hydrogen, halogen, alkyl, alkoxy, nitro, —$SO_2R_4$, carboxyl or hydroxyl, where $R_4$ is —$NH_2$, —NHR′, —NR′R″, —OR′ or —O—aryl in which R′ and R″ are alkyl or alkoxy; $R_2$ is selected from hydrogen or halogen, and X is hydrogen or alkyl, provided that when $R_2$ is halogen then both $R_1$ and $R_3$ are hydrogen and X is alkyl.

The above biguanides are utilized in lens disinfecting and/or preservative solutions in microbicidally effective concentrations. The antibacterial-antifungal action of the biguanide-containing solutions described herein may also be supplemented by the addition of other germicidal agents. Because the overall germicidal activity of such combinations may in some instances be greater than when each is used separately, the concentration of total disinfectant in solution under such circumstances can be lowered, further reducing the potential for binding, concentrating and adverse toxic effects.

DESCRIPTION OF PREFERRED EMBODIMENTS

This invention relates to methods of disinfecting and/or preserving most contact lenses, including hard and soft lenses, as well as the newer hard gas permeable type contact lenses, such as described in U.S. Pat. No. 4,327,203. The term "soft contact lens" as used herein generally refers to contact lenses which readily flex under small amounts of force and return to their original shape when the force is released. Typically, soft contact lenses are formulated from poly(hydroxyethyl methacrylate) which has been, in the preferred formulations, cross-linked with ethylene glycol dimethacrylate. For convenience, this polymer is generally known as PHEMA. Soft contact lenses are also made from silicon polymers cross-linked, for example, with dimethyl polysiloxane. Conventional "hard contact lenses", which cover only the cornea of the eye, usually consist of poly(methyl methacrylate) cross-linked with ethylene glycol dimethacrylate.

The disinfecting solutions employed in the methods of the present invention are effective at low concentrations against a wide spectrum of microorganisms, including but not limited to *S. epidermidis, C. albicans, A. fumigatus,* etc. The solutions contain as their principal microbiocide, a biguanide of the formula:

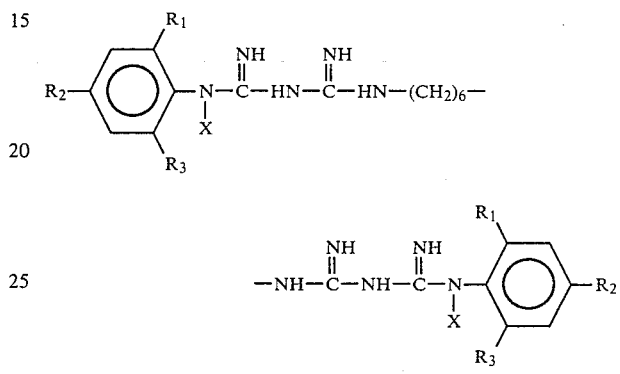

wherein $R_1$ and $R_3$ are independently selected from hydrogen, a halogen from the group of chlorine, bromine, iodine or fluorine, alkyl having from 1 to about 6 carbon atoms, alkoxy having 1 to about 6 carbon atoms, nitro, —$SO_2R_4$, carboxyl and hydroxyl, where $R_4$ is —$NH_2$, —NHR′, —NR′R″, —OR′ or —O—aryl in which R′ and R″ are $C_1$ to $C_6$ alkyl or alkoxy and aryl includes both substituted and unsubstituted phenyl, naphthyl and anthryl; $R_2$ is hydrogen or a halogen selected from chlorine, bromine, iodine or fluorine, and X is hydrogen or $C_1$ to $C_5$ alkyl with the proviso that when $R_2$ is halogen then $R_1$ and $R_3$ are hydrogen and X is alkyl.

More particularly, within the above group of monomeric biguanides most preferred are those wherein ring substitutions for the halogens are chlorine or bromine; lower alkyls like methyl, ethyl, propyl and isopropyl; lower alkoxy such as methoxy and ethoxy. Within this preferred group are compounds in which $R_1$ and $R_3$ are hydrogen, $R_2$ is chlorine or bromine and X is a lower alkyl radical.

In addition to the foregoing, the present invention also includes water-soluble salts and free bases, as for example, hydrochloride and borate salts, acetate, gluconate, sulfonate, tartrate, citrate salts, etc.

Specific representative embodiments of biguanides for use in the contact lens disinfectant methods include free bases and water soluble salts wherein:

| $R_1$ | $R_2$ | $R_3$ | X |
|---|---|---|---|
| H | Cl | H | $CH_3$— |
| H | Br | H | $CH_3$—$CH_2$— |
| Cl | H | H | H |
| Cl | H | Cl | H |
| —$OCH_3$ | H | —$OCH_3$ | H |
| —$NO_2$ | H | H | H |
| —OH | H | —OH | $CH_3$— |

| R₁ | R₂ | R₃ | X |
|---|---|---|---|
| $-\underset{\underset{O}{\|}}{\overset{\overset{O}{\|}}{S}}-CH_3$ | H | H | H |
| H | H | H | H |
| H | H | H | CH₃— |

The monomeric biguanides may be prepared according to methods well documented in the literature. For example, Rose et al, *J. Chem. Soc.*, pp. 4422–4425 (1956) describe methods for the preparation of various bisdiguanides having antibacterial activity, including chlorhexidine. Generally, the compounds are prepared either by condensing one mole of a biscyanoguanidine with two moles of an amine hydrochloride, or conversely by the interaction of two moles of an N-arylcyanoguanidine with one of a diamine salt. The following reactions illustrate the general method for their preparation:

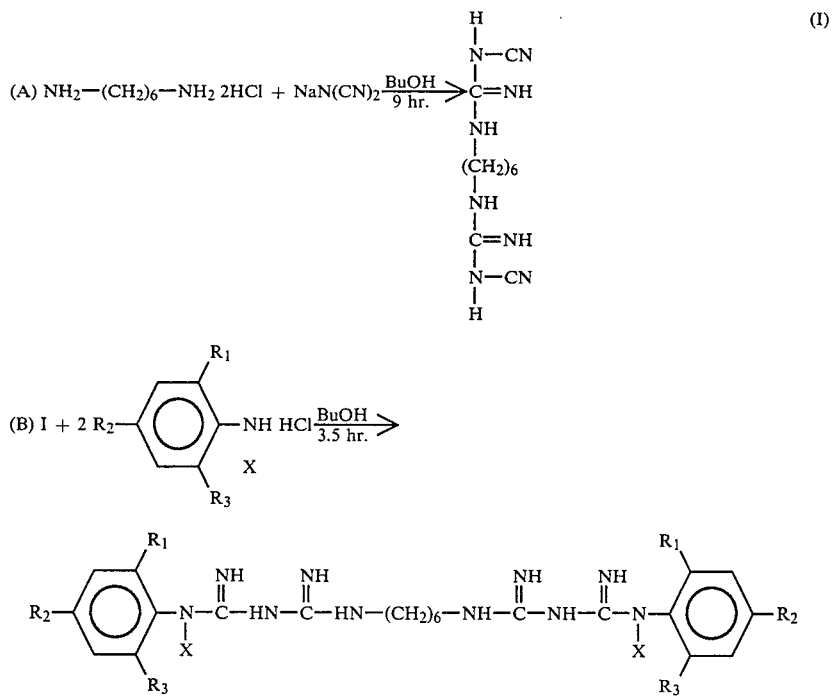

Reaction (A) involving the preparation of 1,6-di(N³-cyano-N¹-guanidino)hexane is carried out using a hexamethylene bridged system. 1,6-diaminohexane dihydrochloride, prepared by dissolving the appropriate amine in ether and then bubbling hydrochloric acid gas into the solution, precipitating out the amine salt which after being filtered is reacted with sodium dicyanimide dihydrochloride in n-butanol. The mixture is refluxed for up to 9 hours. The resultant product is isolated and purified. The product of reaction (A) is then reacted with the appropriate arylamine hydrochloride in reaction (B) to yield the bisbiguanide. Alternatively, the bisbiguanides may be condensed by heating the arylamine hydrochloride with the product of reaction (A) without solvent at 160° C. for 2 hours.

The solutions are generally effective with biguanide concentrations as low as 0.00001 weight percent. More particularly, the disinfectant and preservatives solutions will contain from about 0.00001 to about 7 weight percent of the active biguanide.

It has also been discovered that the microbicidal activity of the solutions may in some cases be enhanced or spectrum of activity broadened through the use of a potentiating amount of a second disinfectant or germicidal agent. Under such circumstances, the total concentration of disinfectant required when the biguanide is used in combination with other germicidal agents may be lowered further due to complimentary microbicidal activity which is most desirable in achieving the lowest possible potential for lens binding, concentrating and eye tissue inflammation. Thus, the effective concentration of biguanide may be lowered to about 0.00001 weight percent and up to 5 weight percent.

The second disinfectant/germicide can be employed as a solution preservative, but it may in some instances also function to potentiate, compliment or broaden the spectrum of microbicidal activity of the biguanide disinfectant. This includes microbicidally effective amounts of germicides which are compatible with and do not precipitate in the presence of the biguanide, and comprises concentrations ranging from about 0.00001 to about 0.5 weight percent, and more preferably, from about 0.0001 to about 0.1 weight percent. Suitable complimentary germicidal agents include, but are not limited to thimerosal, sorbic acid, 1,5-pentanedial, alkyl triethanolamines, phenylmercuric salts, e.g. nitrate, borate, acetate, chloride and mixtures thereof. Other germicidal compounds and salts may be used. Suitable salts are soluble in water at ambient temperature to the extent of at least 0.5 weight percent. These salts include the gluconate, isothionate(2-hydroxyethanesulfonate), formate, acetate, glutamate, succinamate, monodiglycollate, dimethanesulfonate, lactate, diisobutyrate and glucoheptonate.

Further embodiments of potentiating or complimentary disinfecting agents for use with the biguanides also include certain quaternary ammonium compounds which possess a generally wide spectrum of bactericidal activity and wetting properties. Representative examples of the quaternary ammonium compounds are compositions comprised of balanced mixtures of n-alkyl dimethyl benzyl ammonium chlorides and n-alkyl dimethyl ethylbenzyl ammonium chlorides. Such dual quaternary ammonium compositions are described in U.S. Pat. Nos. 3,525,793 and 3,472,939 and are commercially available from Onyx Chemical Company, Jersey City, N.J., under the trademark BTC 2125M.

The aqueous solutions for use in the methods of the present invention are preferably adjusted with tonicity agents to approximate the osmotic pressure of normal lacrimal fluids which is equivalent to a 0.9 percent solution of sodium chloride or 2.5 percent of glycerol solution. Solutions are made substantially isotonic with physiological saline used alone or in combination, otherwise if simply blended with sterile water and made hypotonic the treated lenses may adhere tightly to the cornea. Correspondingly, excess saline may result in the formation of a hypertonic solution which will cause stinging and eye irritation.

The aqueous isotonic solutions with optional germicidal agents are useful disinfectants for both hard and soft contact lenses without any further additives. However, the solutions of the present invention may be formulated into specific contact lens care products, such as wetting solutions, soaking solutions, cleaning and conditioning solutions, as well as all purpose type lens care solutions by the addition of various buffering agents, optional cleaning and wetting agents, sequestering agents, viscosity builders, etc. and mixtures thereof. Such additives make the solutions in many instances more acceptable to the user in terms of greater comfort. However, the additives must be non-toxic and compatible with contact lenses.

Suitable buffers include, for example, sodium or potassium citrate, citric acid, boric acid, sodium bicarbonate and various mixed phosphate buffers, including combinations of $Na_2HPO_4$, $NaH_2PO_4$ and $KH_2PO_4$. Generally, buffers may be used in amounts ranging from about 0.05 to 2.5 percent, and more preferably, from about 0.1 to 1.5 percent (w/v).

When used, neutral or non-ionic surfactants impart cleaning and conditioning properties and are usually present in amounts up to 15 weight percent. The surfactant should be soluble in the lens care solution, non-irritating to eye tissues and will usually have a hydrophile-lipophile balance (HLB) of 12.4 to 18.8. Satisfactory non-ionic surfactants include polyethylene glycol esters of fatty acids, e.g. coconut, polysorbate, polyoxyethylene or polyoxypropylene ethers of higher alkanes ($C_{12}$-$C_{18}$). Examples of the preferred class includes polysorbate 20 (available under the trademark Tween 20), polyoxyethylene (23) lauryl ether (Brij ®35), polyoxyethylene (40) stearate (Myrj ®52), polyoxyethylene (25) propylene glycol stearate (Atlas ®G 2612).

One non-ionic surfactant in particular consisting of a poly(oxypropylene)-poly(oxyethylene) adduct of ethylene diamine having a molecular weight from about 7,500 to about 27,000 wherein at least 40 weight percent of said adduct is poly(oxyethylene) has been found to be particularly advantageous for use in cleaning and conditioning both soft and hard contact lenses when used in amounts from about 0.01 to about 15 weight percent. Such surfactants are available from BASF-Wyandotte under the registered trademark—Tetronic.

In addition to the foregoing buffering agents, cleaning and wetting agents, in some instances it may be desirable to include sequestering agents in the contact lens care solution in order to bind metal ions which might otherwise react with protein deposits and collect on lens surfaces. Ethylenediaminetetraacetic acid (EDTA) and its salts (disodium) are prepared examples. They are usually added in amounts ranging from about 0.1 to about 2.0 weight percent.

It may also be desirable to include water-soluble viscosity builders in the biguanide containing lens disinfectant solutions. Because of their demulcent effect, viscosity builders have a tendency to enhance the lens wearer's comfort by means of a film on the lens surface cushioning impact against the eye. Included among the water-soluble viscosity builders are the cellulose polymers, like hydroxyethyl or hydroxypropyl cellulose, carboxymethyl cellulose, and the like. Such viscosity builders may be employed in amounts ranging from about 0.01 to about 4.0 weight percent, or less.

The aqueous solutions can be effectively used in disinfecting contact lenses by any of the well recognized methods. For example, lenses may be treated by the "cold" soaking method at room temperature for a time period sufficient to disinfect the lenses which is usually a period ranging from 4 to 12 hours. The lenses are then removed from the solution, washed in preserved isotonic saline solution and then replaced on the eyes.

In addition to the cold soaking method, the solutions disclosed herein are adaptable for use in most types of disinfecting equipment, such as ultrasonic cleaners. Because the solutions are also stable when heated, they are adaptable for use with high temperature disinfecting methods. Typically, lenses are heated in the range of 80° to 90° C. in a disinfecting unit containing the solution for a time period of at least 10 minutes, removed and rinsed with isotonic saline.

The following specific examples demonstrate the methods of the invention. However, it is to be understood that these examples are for illustrative purposes only and do not purport to be wholly definitive as to conditions and scope.

EXAMPLE I

Synthesis of 1,6-di($N^3$-Cyano-$N^1$-guanidino)hexane 94.5 g (0.5 mole) of 1,6-diaminohexane dihydrochloride mixed with 103 g (1 mole) of sodium dicyanimide is added to 700 ml of n-butanol. The mixture is refluxed with stirring for 8.5 hours. The reaction mixture is then cooled with ice. The product is precipitated, filtered off, washed with ice water and dried. The product has a melting point of 200°–203° C. It is recrystallized from aqueous methanol (1.5 liter of methanol plus 2.5 liter of water). The above-identified material thus obtained (116.5 g, 0.47 mole, 94% yield) had a m.p. 206°–208° C.

EXAMPLE II

Synthesis of N,$N^1$-bis(o-chlorophenyl)-3,12-diimino-2,4,11,13 tetraaza-tetradecane diimidamide dihydrochloride 6.0 g (0.024 mole) of the product of Example I and 8.0 g (0.048 mole) of ortho-chloroaniline hydrochloride are added to 60 ml of 2-ethoxyethanol and the whole mixture is refluxed with stirring for 11.5 hours. On cooling, a small amount of material is separated with a m.p.>300° C., which is rejected. The filtrate is evaporated to dryness (rotavap) and the residue consisting of 1.26 g (0.0022 mole) is recrystallized from water (25 ml) and yields 1.0 g (7% yield) of the above-identified product having a m.p. 231°-234° C.

EXAMPLE III

N,N¹-dimethyl-bis(p-chlorophenyl)-3,12-diamino-2,4,11,13 tetraaza-tetradecane diimidamide (w/v). In vitro microbicidal activity of the solutions is determined by exposing *S. epidermidis*, *C. Albicans* and *A. fumigatus* to 20 ml of each solution at room temperature for 5 hours. Subsequently, an aliquot sample of each is placed on an agar plate and incubated for 48 hours at elevated temperatures. At the conclusion of the incubation period the plates are examined for the development of colonies. The following table provides the results of the in vitro studies.

TABLE

| DISINFECTANT/ PRESERVATIVE | CONCENTRATION- % (w/v) | *S. epidermidis* | *C. albicans* | *A. fumigatus* |
|---|---|---|---|---|
| | | (Average Log Reduction) | | |
| N,N¹—Bis(o-chlorophenyl)-3,12-diimino-2,4,11,13-tetraaza-tetradecane diimidamide.2 HCl | 0.1 | 6.5 | 4.8 | 1.6 |
| | 0.01 | 6.0 | 4.5 | 1.8 |
| | 0.001 | 6.1 | 3.2 | 0.7 |
| N,N¹—dimethyl-bis(p-chlorophenyl)-3,12-diimino-2,4,11,13-tetraaza-tetradecane diimidamide.2 HCl | 0.1 | 6.5 | 6.0 | 1.4 |
| | 0.01 | 6.0 | 6.1 | 1.9 |
| | 0.001 | 4.2 | 1.5 | 0.9 |
| N,N¹—bisphenyl-3,12-diimino-2,4,11,13-tetraaza-tetradecane diimidamide.2 HCl | 0.1 | 6.4 | 6.0 | 2.0 |
| | 0.01 | 6.0 | 4.8 | 2.4 |
| | 0.001 | 3.3 | 1.6 | 0.6 |
| N,N¹—bis(p-chlorophenyl)-3,12 diimino-2,4,11,13-tetraaza-tetradecane diimidamide.2 HCl (chlorhexidine dihydrochloride) | 0.001 | 3.7 | 0.3 | 0.1 | dihydrochloride 6.0 g (0.024 mole) of the product of Example I and 8.6 g (0.048 mole) of N-methyl-p-chloroaniline hydrochloride are heated in an oil bath at 160° C. (±5° C.) for 2 hours. The mixture is cooled and dissolved in 50 ml of ethanol to which is added 50 ml of ethyl acetate. The crude precipitate weighs 5.5 g (0.009 mole) and melts at 159°-162° C. After recrystallization from water, it is obtained as 3.3 g (0.005 mole, 21% yield) having a m.p. 171°-173° C.

EXAMPLE IV

An aqueous contact lens disinfecting solution is prepared having the following formulation:

| | percent (w/v) |
|---|---|
| N,N¹—Bis(o-chlorophenyl)-3,12-diimino-2,4,11,13 tetraaza-tetradecane diimidamide dihydrochloride | 0.0025 |
| Boric acid and sodium borate to maintain pH 7.2 | 0.103 |
| Na₂ EDTA | |
| Tonicity adjusted with isotonic saline containing 0.9% NaCl | 100.0 |
| Dist. water qs | |

The solution is prepared by dissolving the sodium borate in approximately 80 percent of the distilled water. The disodium EDTA is then added to the sodium borate solution, followed by dissolving the boric acid and sodium chloride therein. The biguanide is then added followed by the balance of the distilled water. The solution is sterilized by forcing through a 0.22 micron cellulose acetate filter by means of a peristaltic pump and packaged in sterilized plastic containers.

EXAMPLE V

A group of aqueous biguanide solutions are prepared most with concentrations of 0.1; 0.01 and 0.001 percent The foregoing in-vitro studies demonstrate the improved antimicrobial activity of the biguanide isomers over p-chloro derivative (chlorohexidine).

While the invention has been described in conjunction with specific examples thereof, this is illustrative only. Accordingly, many alternatives, modifications and variations will be apparent to those skilled in the art in light of the foregoing description, and it is therefore intended to embrace all such alternatives, modifications and variations as to fall within the spirit and broad scope of the appended claims.

What is claimed is:

1. A method of disinfecting and/or preserving contact lenses which comprises treating said lenses with an antimicrobial amount of a solution comprising a biguanide or its water soluble salt of the formula:

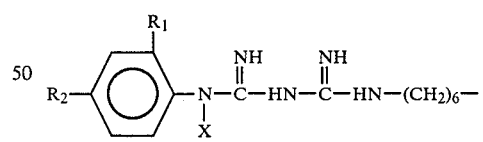

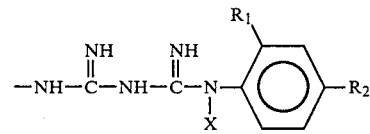

wherein $R_1$ and $R_2$ are hydrogen or halogen and X is hydrogen or alkyl, provided that when $R_2$ is halogen then $R_1$ is hydrogen and X is alkyl.

2. The method of claim 1 wherein $R_1$ and $R_2$ are hydrogen, chlorine or bromine and X is hydrogen or lower alkyl, provided that when $R_2$ is chlorine or bromine then $R_1$ is hydrogen and X is lower alkyl.

3. The method of claim 1 wherein $R_1$ is halogen and $R_2$ is hydrogen.

4. The method of claim 3 wherein $R_1$ is chlorine and $R_2$ and X are each hydrogen.

5. The method of claim 4 wherein $R_1$, $R_2$ and X are hydrogen.

6. The method of claim 1 wherein $R_1$ is hydrogen, $R_2$ is halogen and X is alkyl.

7. The method of claim 6 wherein $R_2$ is chlorine and X is lower alkyl.

8. The method of claim 7 wherein X is methyl.

9. The method of claim 1 wherein the biguanide-containing solution includes a tonicity and a buffering agent.

10. A method of disinfecting and/or preserving contact lenses which comprises treating said lenses with an effective amount of a solution comprising a microbicidally effective mixture of a biguanide and at least one other germicidal agent, said biguanide having the formula:

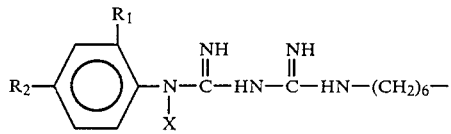

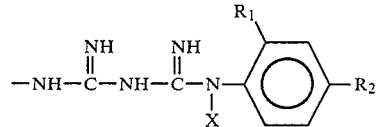

wherein $R_1$ and $R_2$ are hydrogen or halogen and X is hydrogen or alkyl, provided that when $R_2$ is halogen then $R_1$ is hydrogen and X is alkyl.

11. The method of claim 10 wherein $R_1$ and $R_2$ are hydrogen, chlorine or bromine and X is hydrogen or lower alkyl, provided that when $R_2$ is chlorine or bromine $R_1$ is hydrogen and X is lower alkyl.

12. The method of claim 10 wherein the germicidal agent is a member selected from the group consisting of thimerosal, sorbic acid and phenylmercuric salts.

13. The method of claim 12 wherein the solution includes tonicity and buffering agents.

14. The method of claim 10 wherein $R_1$ is hydrogen, $R_2$ is halogen and X is alkyl.

15. The method of caim 14 wherein $R_2$ is chlorine and X is lower alkyl.

16. The method of claim 15 wherein X is methyl.

17. The method of claim 10 wherein $R_1$ is halogen and $R_2$ is hydrogen.

18. The method of claim 17 wherein $R_1$ is chlorine and $R_2$ and X are each hydrogen.

19. The method of claim 10 wherein $R_1$, $R_2$ and X are hydrogen.

* * * * *